(12) United States Patent
Bulver

(10) Patent No.: US 6,494,907 B1
(45) Date of Patent: Dec. 17, 2002

(54) BRAIDED STENT

(75) Inventor: Julie M. Bulver, Plymouth, MN (US)

(73) Assignee: IntraTherapeutics, Inc., St. Paul, MN (US)

( * ) Notice: Subject to any disclaimer, the term of this patent is extended or adjusted under 35 U.S.C. 154(b) by 0 days.

(21) Appl. No.: 09/067,665

(22) Filed: Apr. 28, 1998

(51) Int. Cl.$^7$ .................................................. A61F 2/06
(52) U.S. Cl. ..................... 623/1.22; 623/1.53; 623/1.11
(58) Field of Search .............................. 623/1, 12, 1.11, 623/1.14, 1.15, 1.22; 87/2, 7, 13, 33; 128/898

(56) References Cited

U.S. PATENT DOCUMENTS

| | | | |
|---|---|---|---|
| 3,868,956 A | 3/1975 | Alfidi et al. ............... 128/345 |
| 4,517,687 A | 5/1985 | Liebig et al. ................... 3/1.4 |
| 4,530,113 A | 7/1985 | Matterson ..................... 623/1 |
| 4,553,545 A | 11/1985 | Maass et al. ............... 128/341 |
| 4,649,922 A | 3/1987 | Wiktor ........................ 128/344 |
| 4,655,771 A | 4/1987 | Wallsten ........................ 623/1 |
| 4,760,849 A | 8/1988 | Kropf ......................... 128/341 |
| 4,771,773 A | 9/1988 | Kropf ..................... 128/303 R |
| 4,851,009 A | 7/1989 | Pinchuk ......................... 623/66 |
| 4,886,062 A | 12/1989 | Wiktor ........................ 128/343 |
| 4,969,458 A | 11/1990 | Wiktor ........................ 606/194 |
| 5,057,092 A | 10/1991 | Webster, Jr. ................. 604/282 |
| 5,061,275 A | 10/1991 | Wallsten et al. ............... 623/1 |
| 5,064,435 A | 11/1991 | Porter ......................... 623/12 |
| 5,217,495 A | * 6/1993 | Kaplan et al. ................. 623/1 |
| 5,342,348 A | 8/1994 | Kaplan ..................... 604/891.1 |
| 5,366,504 A | 11/1994 | Andersen et al. ............. 623/11 |
| 5,370,682 A | * 12/1994 | Schmitt ......................... 623/1 |
| 5,372,600 A | 12/1994 | Beyar et al. ................. 606/108 |
| 5,449,372 A | 9/1995 | Schmaltz et al. ........... 606/198 |
| 5,545,208 A | * 8/1996 | Wolff et al. .................... 623/1 |
| 5,575,818 A | 11/1996 | Pinchuk ......................... 623/1 |
| 5,591,222 A | 1/1997 | Susawa et al. ................. 623/1 |
| 5,597,378 A | 1/1997 | Jervis ........................... 606/78 |
| 5,618,298 A | 4/1997 | Simon ......................... 606/194 |
| 5,632,746 A | 5/1997 | Middleman et al. .......... 606/78 |
| 5,645,559 A | 7/1997 | Hachtman et al. .......... 606/198 |
| 5,674,276 A | 10/1997 | Andersen et al. .............. 623/1 |
| 5,718,159 A | 2/1998 | Thompson .................... 87/33 |
| 5,749,919 A | * 5/1998 | Blane ............................. 623/1 |
| 5,758,562 A | * 6/1998 | Thompson .................... 87/33 |
| 5,871,535 A | * 2/1999 | Wolff et al. .................... 623/1 |
| 5,893,867 A | * 4/1999 | Bagaoisan et al. .......... 606/198 |
| 5,961,547 A | * 10/1999 | Razavi ........................... 623/1 |
| 5,964,797 A | * 10/1999 | Ho ................................. 623/1 |
| 6,241,691 B1 | * 6/2001 | Ferrera et al. ............... 600/585 |

FOREIGN PATENT DOCUMENTS

| | | | |
|---|---|---|---|
| DE | 195 16 060 A1 | 11/1996 | |
| EP | 0 122 744 | 3/1984 | ............ A61F/1/00 |
| EP | 0 740 928 A2 | 11/1996 | |
| WO | WO 91/12779 | 9/1991 | |
| WO | WO 95/29646 | 11/1995 | ............ A61F/2/04 |
| WO | WO 97/13475 | 4/1997 | |
| WO | WO 97/25000 | 7/1997 | |
| WO | WO 97/25002 | 7/1997 | |

OTHER PUBLICATIONS

*Braidmaking* by Barbara Pegg, Published 1990, A&C Black Publishers Ltd., London pp. 9–17.

* cited by examiner

*Primary Examiner*—David H. Willse
*Assistant Examiner*—Suzette J. Jackson
(74) *Attorney, Agent, or Firm*—Merchant & Gould P.C.

(57) ABSTRACT

A radially expandable stent for implantation within a body vessel, comprising one or more continuous, discrete, metal strands. At least three strands repeatedly cross over each other to form a bundle. The strands are joined at the proximal and distal end such that the strands are free to adjust their position relative to each other in response to compression forces. One or more bundles are wound together to form an elongate hollow tube.

10 Claims, 4 Drawing Sheets

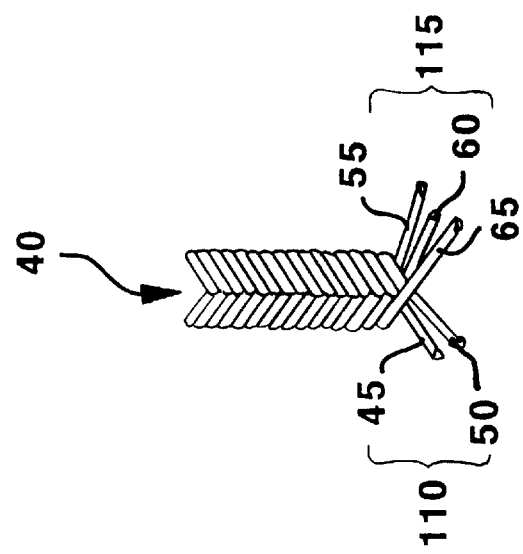
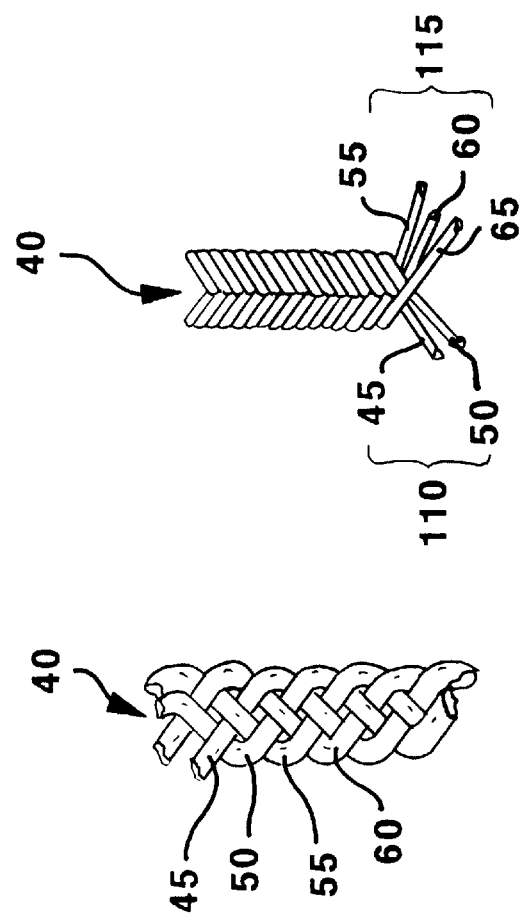
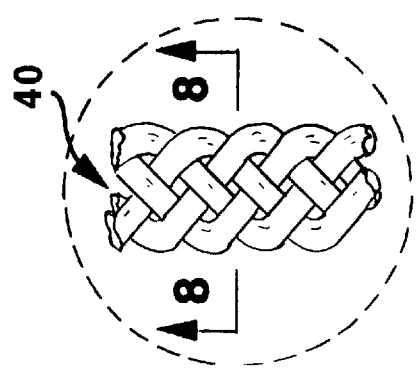
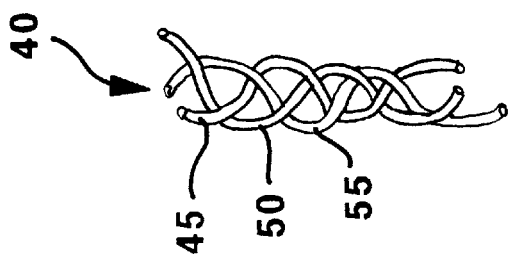
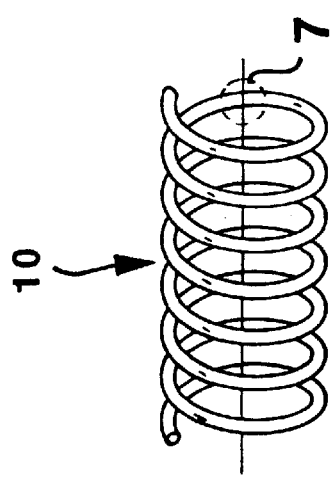

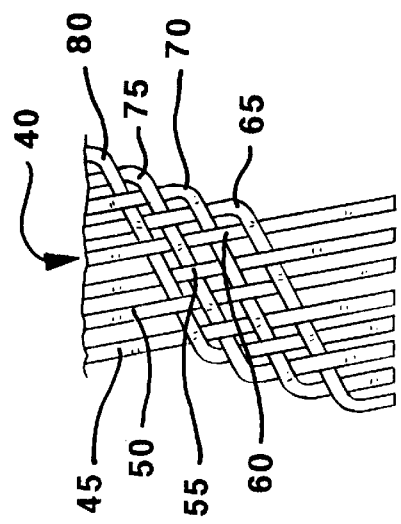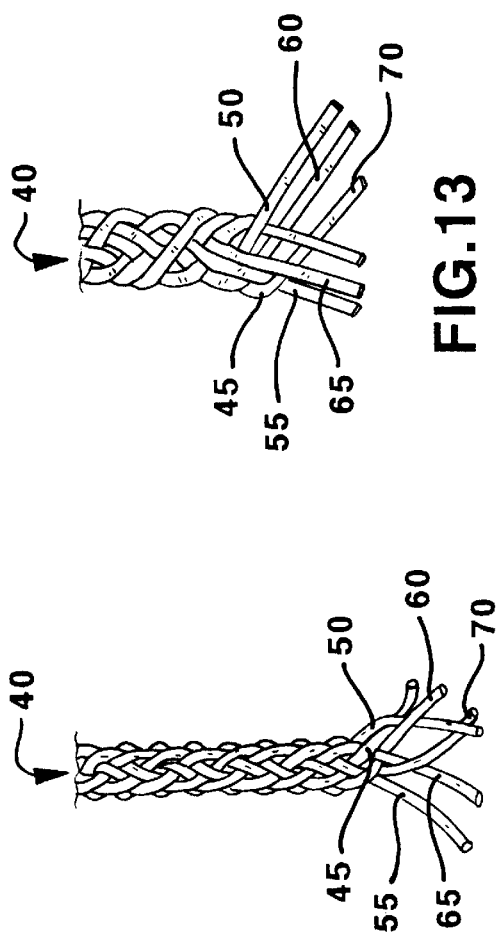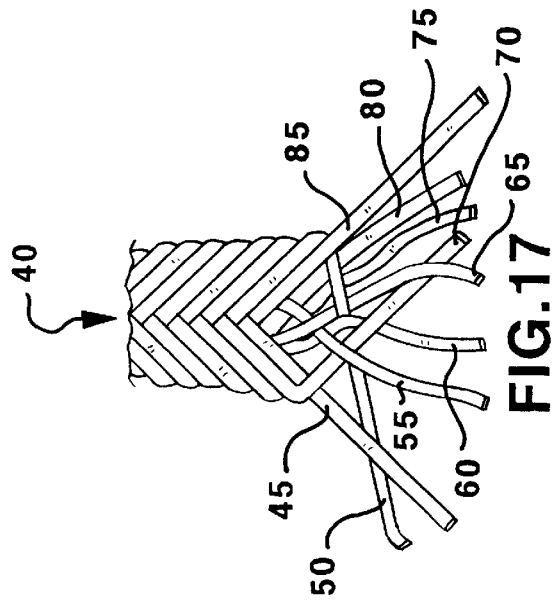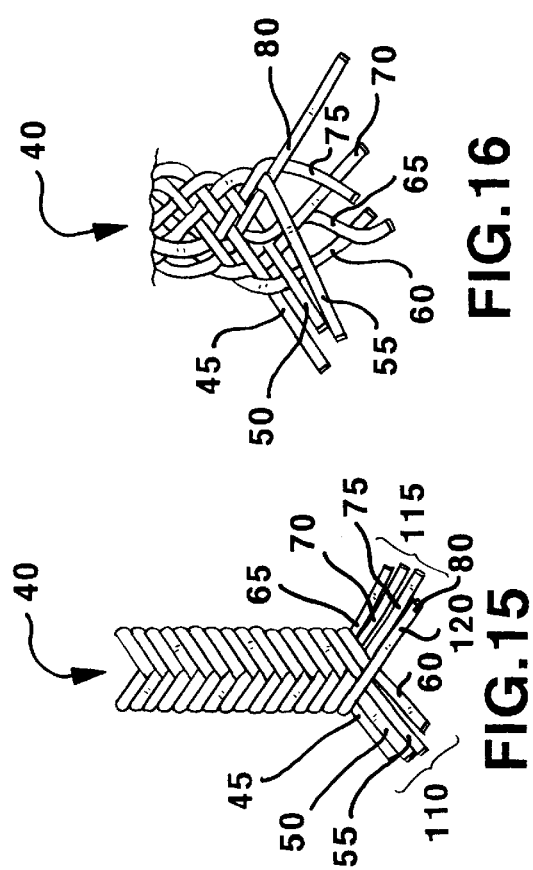

BRAIDED STENT

FIELD OF THE INVENTION

The present invention relates to intravascular stent implants for maintaining vascular patency in humans and animals and more particularly to a stent in the form of a braided stent.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. It has also been shown that the use of intravascular stents can measurably decrease the incidence of restenosis after angioplasty thereby reducing the likelihood that a secondary angioplasty procedure or a surgical bypass operation will be necessary.

An implanted prosthesis such as a stent can preclude additional procedures and maintain vascular patency by mechanically supporting dilated vessels to prevent vessel reclosure. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

A typical stent is a cylindrically shaped wire formed device intended to act as a permanent prosthesis. A typical stent ranges from 5 mm to 50 mm in length. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a catheter bearing a stent which has been secured to the catheter such as in U.S. Pat. No. 5,372,600 to Beyar et al. which is incorporated herein by reference in its entirety.

The stent must be reduced in size to facilitate its delivery to the intended implantation site. A coil stent is delivered by winding it into a smaller diameter and fixing it onto a delivery catheter. When the device is positioned at the desired site, the coil is released from the catheter and it either self-expands by its spring force or it is otherwise mechanically expanded to the specified dimension.

As with many stents, the deformation of the stent when it is assembled on the delivery catheter causes a strain in the stent material. If the strain is too large the material will experience plastic deformation to such an extent that the stent will not recover to the intended dimensions following deployment. This is true of superelastic or pseudoplastic alloys such as disclosed in U.S. Pat. No. 5,597,378 issued to Jervis, which is incorporated herein by reference in its entirety. Thus a maximum allowable strain based on material is a limiting parameter in stent design.

Two parameters influence the amount of strain a stent will experience during the deformation described above. The first is the degree of deformation applied to the stent and the second is the thickness of the stent material. For a given deformation, the strain experienced by a material is proportional to the thickness of the material. Since it is desirable to deliver a stent on the smallest delivery system possible it follows that the thickness of the stent material should be reduced to keep the strain within acceptable parameters. When forming a stent with a single solid strand (such a length of solid wire), a limit will be reached where the thickness of material becomes so small that the stent will meet the maximum allowable strain but will no longer have the hoop strength to provide adequate scaffolding.

Current helical coil stents are delivered on the smallest profile catheter that the stent will allow. Strain on the stent during assembly on the catheter is the limiting factor with stents made from solid round or flat wire helical coil stents.

U.S. Pat. No. 5,342,348 to Kaplan for "Method and Device for Treating and Enlarging Body Lumens" discloses a single helically wound strand and two counterwound delivery matrix filaments. A two stranded stent is shown in U.S. Pat. No. 5,618,298 to Simon for "Vascular Prosthesis Made of Reasorbable Material".

Mesh stents are disclosed in U.S. Pat. No. 5,061,275 to Wallsten et al. for "Self-Expanding Prosthesis", U.S. Pat. No. 5,064,435 to Porter for "Self-Expanding Prosthesis Having Stable Axial Length", U.S. Pat. No. 5,449,372 to Schmaltz et al. for "Temporary Stent and Methods for Use and Manufacture", U.S. Pat. No. 5,591,222 to Susawa et al. for "Method of Manufacturing a Device to Dilate Ducts in Vivo", U.S. Pat. No. 5,645,559 to Hachtmann et al. for "Multiple Layer Stent", U.S. Pat. No. 5,718,169 to Thompson for "Process for Manufacturing Three-Dimensional Braided Covered Stent".

Woven mesh stents typically have warp and weft members as disclosed in U.S. Pat. No. 4,517,687 to Liebig et al. for "Synthetic Woven Double-Velour Graft", U.S. Pat. No. 4,530,113 to Matterson for "Vascular Grafts with Cross-Weave Patterns", U.S. Pat. No. 5,057,092 to Webster for "Braided Catheter with Low Modulus Warp" and EP 122, 744 to Silvestrini for "Triaxially-braided Fabric Prosthesis". The warp strands are typically the strands in the longitudinal direction on a prosthesis. The weft strands are typically the strands which are shuttled through warp strands to form a two dimensional array.

WO 95/29646 to Sandock for a "Medical Prosthetic Stent and Method of Manufacture" discloses a geometric pattern of cells defined by a series of elongate strands extending to regions of intersection and interlocking joints at regions of intersections formed by a portion of at least one strand being helically wrapped about a portion of another.

Various helical stents are known in the art. U.S. Pat. No. 4,649,922 to Wiktor for "Catheter Arrangement Having A Variable Diameter Tip and Spring Prosthesis" discloses a linearly expandable spring-like stent. U.S. Pat. No. 4,886,062 to Wiktor for "Intravascular Radially Expandable Stent and Method of Implant" discloses a two-dimensional zig-zag form, typically a sinusoidal form. U.S. Pat. No. 4,969,458 to Wiktor for "Intracoronary Stent and Method of Simultaneous Angioplasty and Stent Implant" discloses a stent wire coiled into a limited number of turns wound in one direction then reversed and wound in the opposite direction with the same number of turns, then reversed again and so on until a desired length is obtained.

Braiding is a well known craft. See Braidmaking by Barbara Pegg, published by A & C Black Ltd, 35 Bedford Row, London WC1R 4JH, pp. 9–16 which is hereby incorporated by reference.

It is an object of the invention to produce a stent which has the ability to tolerate greater deformations, yet has a smaller profile to permit the use of a smaller delivery system thereby reducing the amount of trauma experienced by the patient. It is a further object of the invention to produce a stent which would recover to specified dimensions with maximized radial hoop strength and resistance to lateral force.

SUMMARY OF THE INVENTION

The present invention is accomplished by providing an apparatus for a radially expandable stent for implantation within a body vessel, comprising one or more continuous, discrete, metal strands. At least three strands repeatedly cross over each other to form a bundle. The strands are joined at the proximal and distal end such that the strands are free to adjust their position relative to each other in response to compression forces. One or more bundles are wound together to form an elongate hollow tube.

BRIEF DESCRIPTION OF THE DRAWINGS

FIG. 6 is an helical coil stent;

FIG. 7 is a detail of the helical coil stent of FIG. 6 using a four stranded cross-over braid;

FIG. 8 is a cross-section of the detail of the bundle of FIG. 7;

FIG. 9 is a three stranded braid;

FIG. 10 is a four stranded cross-over braid;

FIG. 11 is a five stranded braid;

FIG. 12 is a six stranded round braid;

FIG. 13 is an alternate six stranded flat braid;

FIG. 14 is an eight stranded alternating braid;

FIG. 15 is an eight stranded braid;

FIG. 16 is an eight stranded twisted braid;

FIG. 17 is a nine stranded double braid;

DETAILED DESCRIPTION OF THE PREFERRED EMBODIMENTS

Figure 1:
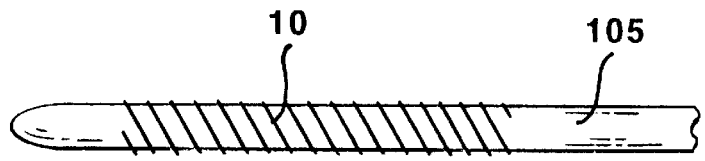
FIG. 1 is a wound down, helical coil stent under strain.

During assembly onto the delivery system (catheter), a helical coil stent 10 is deformed into a reduced diameter 30. This deformation imposes a strain in the stent material. If the strain is too great, the stent 10 will experience plastic deformation to such an extent that the stent will not recover dimensionally to the specified size during deployment. When a stent 10 is reduced to a given catheter diameter 30 the strain experienced by the stent 10 material is proportional to the thickness 35 of the stent material.

The present invention applies to any helical coil stent 10 where deformation is limited by the applied strain. The stent 10 is formed of multiple strands 15. Each strand is continuous and discrete. Multiple strands 15 of material are formed into a bundle 40, each strand 15 having a fine thickness. The resulting hoop strength of the stent 10 formed of one or more bundles 40 will be the cumulative strength of all of the strands 15 in the bundle(s) 40. The strain on the other hand, will be limited to that of a single strand 15. By using multiple fine strands 15 which are formed into a bundle 40, the required strength of the stent 10 can be maintained, while allowing the increased stent 10 to be deformed (wound down) onto a smaller diameter delivery catheter than would otherwise be possible with a single solid strand 15 stent material. Bundles 40 can be formed by braiding or by other means to enable the strands 15 to slide relative to one another when compressed or released; this is necessary to reduce friction. One or more bundles 40 are then formed into the elongate hollow tubular stent 10.

The increased deformation capacity of multiple strands 15 which are formed into a bundle 40 is possible because strain is proportional to a single strand 15 thickness, not the thickness of the bundle 40 of strands 15. The width of the braided bundle 40 of strands is significantly greater than that of a round wire. Multiple strands 15 braided together into a bundle 40 provide support to one another, providing resistance to lateral forces as well as to crushing forces. By increasing the number of strands 15 in the braid, the width can be increased resulting in greater lateral strength. The increase in the number of strands 15 also provides increased radial or "hoop" strength. The braided wire coil stent 10 provides a means to deliver a decreased profile stent while still providing accurate deployment thereby resulting in a less traumatic stent 10 delivery.

When a smaller delivery catheter is needed and the strain on a strand 15 increases, stent 10 deformation will increase when assembling the stent 10 onto a smaller delivery catheter. With a single strand 15, such as a length of wire, a limit will be reached where the following parameters can be optimized no further and the strand 15 thickness can no longer realistically be reduced. These parameters include the delivery catheter size, the hoop strength, the lateral strength.

The preferred number of strands 15 would be unique from one stent application to another. Any number of three or more strands would be possible. A larger diameter 20 stent 10 would generally require more strands 15 than a smaller diameter 20 stent 10 to provide adequate radial and hoop strength. Depending on the anatomy being targeted, a stent 10 might require more strands 15 to increase the resistance to compression, as in a stent 10 intended for implantation in the popliteal artery. Some stents 10 might require fewer strands 15 to minimize the amount of blood contact with metal. Others, such as a biliary stent would require more strands 15 or a flatter braid pattern to provide total coverage of the orifice being stented to prevent tissue in-growth.

The balloon expandable stent 10 can be made of a round wire or of a flat wire using a springy, inert, biocompatible material with high corrosion resistance that can be plastically deformed at low-moderate stress levels. Acceptable materials include tantalum, stainless steel or elgiloy. The preferred embodiment for a self-expanding stent 10 includes superelastic (nickel titanium) NiTi such as Nitinol manufactured by Raychem or Forukawa. Any of the braided patterns could be made from a round wire or from a flat wire.

FIGS. 4–5 and FIGS. 7–20 depict braided stents of 3–6 strands, 8–9 strands, and 11–12 strands with alternative 6 (FIGS. 12 and 13), alternative 8 (FIGS. 14 and 16) and alternative 11 (FIGS. 18 and 19) stranded embodiments. Those skilled in the art would recognize that these examples are not the only braided patterns that could be used for the bundle of strands stent concept. Potentially any braid pattern could be used, as for example, a seven or a ten stranded braid. Preferably, the braid is a flattened braid which is formed into a stent 10 with a flat side of the braid forming the stent cylinder so as to minimize the delivered profile of the stent and to maximize the luminal diameter of the stent.

To braid multiple strands 15, conventional ribbon braiding equipment can be used. After braiding, the helical coil stent 10 could be formed by affixing the ends of the desired length of strands 15 to each other and wrapping the braided bundle 40 around a conventional mandrel to form the desired diameter 20. The ends can be affixed with any welding technique such as, plasma welding, laser welding, RF welding or TIG welding. In addition, brazing, soldering or crimping could be employed to affix the stent ends to each other. By heat treating the assembly the helical coil shape can be "memory set" into the braided bundle 40.

Figure 2:
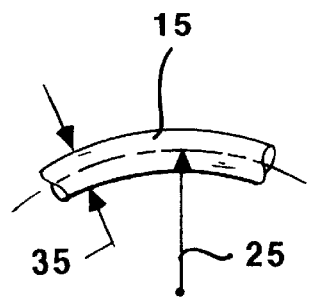
FIG. 2 is a strand with an unstrained radius curvature.
Figure 3:
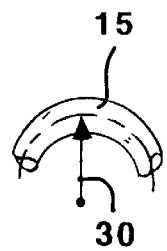
FIG. 3 is a strand with a strained radius curvature.

The following applies whenever devices are deformed and is not limited to stents 10. Stents 10 are placed in a strained state (see FIGS. 1 and 3) during the assembly process where the stents 10 are taken from a free unstrained state (see FIGS. 6 and 2) and are wound onto a delivery catheter 105 at a much smaller diameter. As a braided bundle 40 is formed into a helical coil, the strands 15 may shift with respect to each other. Induced strain is higher when strands 15 stack exactly on top of each other as in FIG. 5 and less if the strands are offset as in FIG. 4.

Strain is highest at the inner edge of the stent coil while in the assembled state (see FIG. 1) and can be represented by the following equation:

Strain=$(d(R_1+R_2-1))÷(2R_1-d)$ where:
  $R_1$ is the unstrained radius of curvature 25
  $R_2$ is the strained radius of curvature 30
  d is the wire strand 35 thickness (wire diameter depending on whether the strand is round or flat) as opposed to the overall stent 10 diameter.

Three stent designs will be mathematically approximated to, for the smallest diameter stent 10 that can be wound down on a delivery catheter without exceeding the 8% strain permitted with Nitinol as the metal. These examples show that the smallest delivery profile achievable is that of a braided multi strand 15 stent 10. All three stents have a nominal outer diameter of 9 mm (0.354 inches) and it is assumed will provide adequate hoop and lateral strength. The material in each example is Nitinol which has a maximum 8% allowable strain.

EXAMPLE I

The first example is a helical coil stent 10 formed from a single member round 0.013 inch wire. A 9 mm outer diameter 20 stent 10 requires a round wire with a minimum diameter of 0.013 inches to provide the necessary hoop strength and lateral stiffness. The applied strain is 8%. For this stent 10 design, the unstrained radius of ad curvature 25 is 0.1705 inches and the outer diameter of the strand 15 is 0.013 inches. Solving the equation for $R_2=R_1÷[[\epsilon÷d](2R_1-d)+1]$ the strained radius of curvature 30 is therefor 0.0565 inches. Solving the equation for $D=2R_2+d$, where D is the outer diameter 20 of the helical coil stent 10 and d is the wire strand thickness or diameter 35, yields a stent outer diameter 20 of 0.126 inches. With the maximum stent 10 outer diameter 20 profile of 0.126 inches, the required introducer size is at least 9.6 French. The delivery of the device would require an introducer sheath or a guide catheter large enough to accommodate the maximum stent 10 outer diameter 20 profile of 0.126 inches or 9.6 French. The stent 10 would therefor pass through a delivery catheter 105 with a 10 French inner diameter of 0.131 inches.

EXAMPLE II

The second example is a 9 mm outer diameter 20 helical coil stent 10 formed from a single strand 10 of 0.008 inch×0.025 inch flat wire. This size wire is wide enough to provide lateral stability which is lost when the thickness of the wire is reduced to 0.008 inches. Using the same method as for the Example 1 round wire above, the unstrained radius of curvature 25 is 0.173 inches and the outer diameter 20 is 0.008 inches. Solving the equation for $R_2=R_1÷[[\epsilon÷d](2R_1-d)+1]$, the strained radius of curvature 30 is therefor 0.087 inches. Solving the equation for $D=2R_2+d$, where D is the outer diameter 20 of the helical coil stent 10 and d is the wire strand thickness or diameter 35, yields a stent outer diameter 20 of 0.087 inches. With the maximum stent 10 outer diameter 20 profile of 0.087 inches, the required introducer size is at least 6.6 French. Due to differences in the wire forming process, the flat wire can only withstand a 7% strain. With a 7% applied strain the maximum device profile is 0.095 inches with a required 7.3 French introducer size. The applicant has been unable to achieve acceptable shape memory results with a strain greater than 7% for flat wire stents. The stents did not return to the nominal diameters following deployment as they were undersized, a function of the flattening process during the raw wire manufacture. With an 8% applied strain, the maximum stent device outer diameter 20 profile is 0.067 inches, with at least a 5.1 French introducer size.

EXAMPLE III

Figure 4:
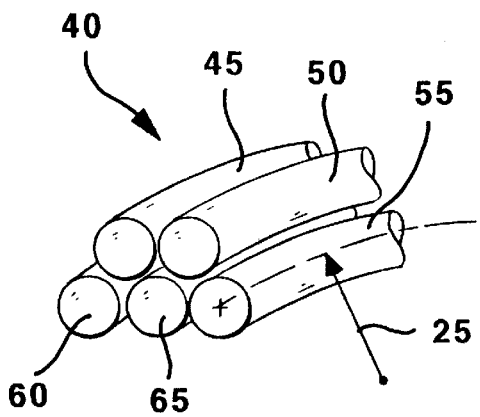
FIG. 4 is a bundle of strands.
Figure 5:
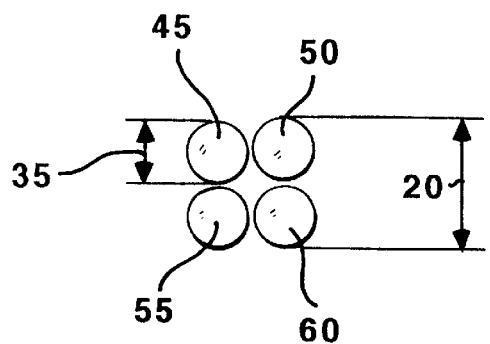
FIG. 5 is a cross-section of a four stranded bundle with worst case stacking.

The third example is a helical coil stent 10 formed from multiple braided 0.005 inch strands 15, as for example five strands 15 seen in FIG. 4 or four strands 15 seen in FIG. 5. Then, $R_{1=}(0.354/2)-3r=(0.354/2\_-3(0.0025)=1.1695$ inches. $R_2=0.267$ the outer diameter, $D=2(R_2=3r)=0.0684$ inches. This corresponds to approximately a 5.2 French introducer.

Figure 20:
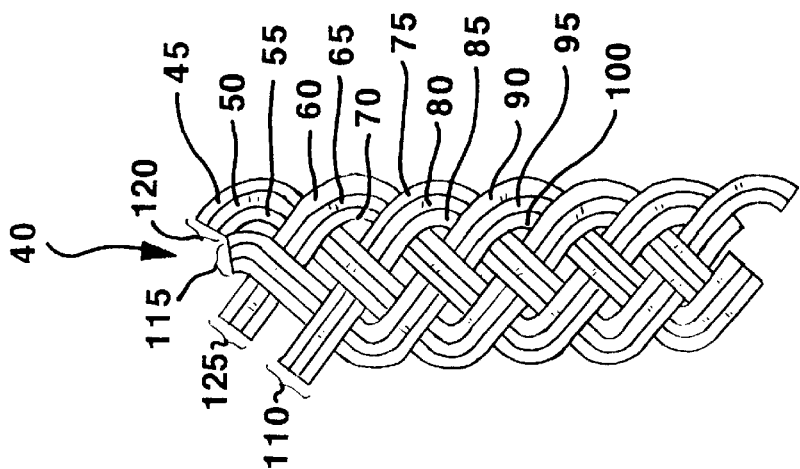
FIG. 20 is a twelve stranded cross-over braid.
Figure 19:
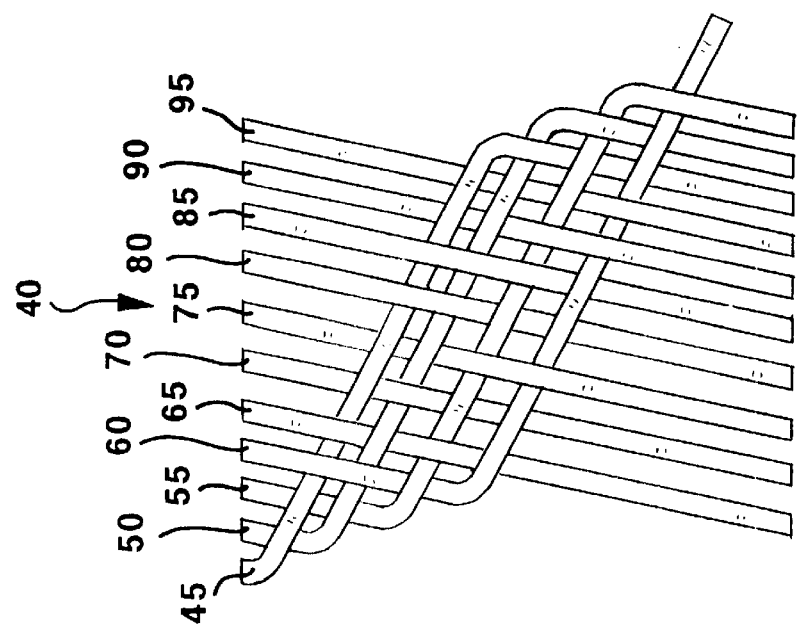
FIG. 19 is an eleven stranded alternating braid.
Figure 18:
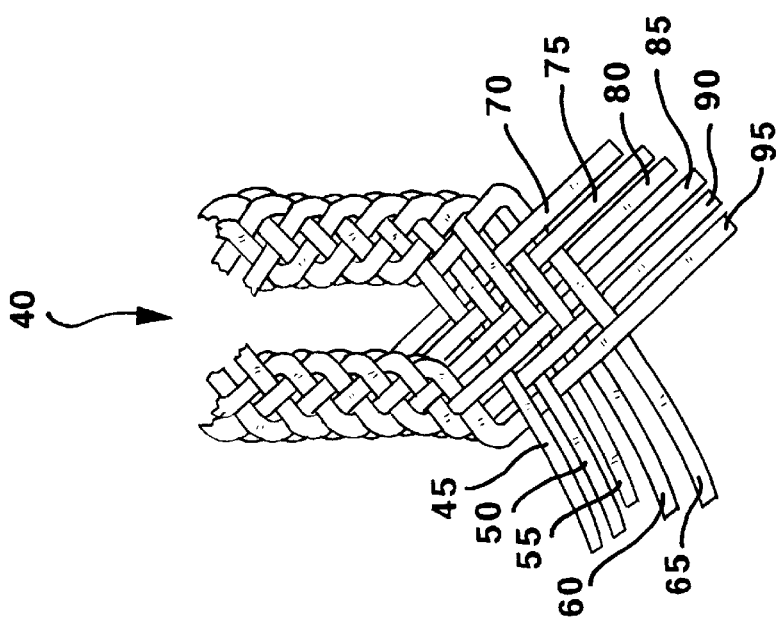
FIG. 18 is an eleven stranded braid.

Braided bundles 40 can be of any number of strands. FIG. 9 is a three stranded braid. Each strand 15 could be a bundle 40 with one to four or more strands. FIG. 10 is a four stranded cross-over braid. Each strand 15 could be a bundle 40 with one to four or more strands. FIG. 11 is a five stranded braid. FIG. 12 is a six stranded round braid. FIG. 13 is a six stranded flat braid. FIG. 14 is an eight stranded alternating braid. FIG. 15 is an eight stranded braid. FIG. 16 is an eight stranded twisted braid. FIG. 17 is a nine stranded double braid. FIG. 18 is an eleven stranded braid. The eleven stranded FIG. 19 is an eleven stranded alternating braid which is braided in the same pattern as the eight stranded FIG. 14 but using three additional strands. Any number of strands, however, could be used in this alternating pattern. FIG. 20 is a twelve stranded cross-over braid made with four bundles 40 with three strands 15 each and braided in the pattern of FIG. 10. Any number of strands could be used in the bundle(s).

The preceding specific embodiments are illustrative of the practice of the invention. It is to be understood, however, that other expedients known to those skilled in the art or disclosed herein, may be employed without departing from the scope of the appended claims.

| No. | Component |
|---|---|
| 10 | Stent |
| 15 | Strand |
| 20 | D - Outer Diameter of Stent |
| 25 | $R_1$ - Unstrained Radius of Curvature |
| 30 | $R_2$ - Strained Radius of Curvature |
| 35 | d - Wire Strand Thickness |
| 40 | Bundle |
| 45 | Strand 1 |
| 50 | Strand 2 |
| 55 | Strand 3 |
| 60 | Strand 4 |
| 65 | Strand 5 |
| 70 | Strand 6 |
| 75 | Strand 7 |
| 80 | Strand 8 |
| 85 | Strand 9 |
| 90 | Strand 10 |
| 95 | Strand 11 |
| 100 | Strand 12 |
| 105 | Delivery Catheter |
| 110 | First Bundle |
| 115 | Second Bundle |
| 120 | Third Bundle |
| 125 | Fourth Bundle |

What is claimed is:

1. A method for implanting a radially expandable stent within a body vessel, which comprises the steps of:
   (a) providing a stent having one or more continuous, discrete, metal strands, each strand having a proximal and a distal end;
   (b) braiding a first, second, and third strand together to form a bundle, wherein a pattern is repeated such that, the first strand crosses over the second strand and under the third strand; the second strand crosses over the third strand and under the first strand; and the third strand crosses under the second strand and over the first strand, the strands being joined at the proximal and distal end such that the strands are free to adjust their position relative to each other in response to compression forces, wherein the bundle is helically wound to form an elongate coil having a first diameter with the coil being releasably secured to a catheter;
   (c) inserting the catheter into the body vessel;
   (d) advancing the catheter through the body vessel until the coil is positioned at a desired site within the body vessel;
   (e) radially expanding at least a portion of the coil to a second diameter within the body vessel at the desired site such that at least the portion of the coil engages and supports the body vessel, with the second diameter being greater than the first diameter;
   (f) releasing the coil from the catheter; and
   (g) removing the catheter from the body vessel.

2. The method according to claim 1 wherein the strands are made of a superelastic metal.

3. The method according to claim 1 wherein the strands are made of a flat metal.

4. The method according to claim 1 wherein the strands are made of a round metal.

5. The method according to claim 1 wherein the first strand comprises a bundle of between one and four strands, the second strand comprises a bundle of between one and four strands and the third strand comprises a bundle of between one and four strands.

6. The method according to claim 1 comprising one or more bundles.

7. The method of claim 1 further including the step of providing a guide catheter, prior to inserting the catheter into the body vessel, the guide catheter sized to receive the catheter with the elongate coil having the first diameter.

8. A method for implanting a radially expandable stent within a body vessel, which comprises the steps of:
   (a) providing a stent having one or more continuous, discrete, metal strands, each strand having a proximal and a distal end;
   (b) braiding a first, second, third, and fourth strand together to form a bundle, wherein a pattern is repeated such that, the first stand crosses over the second strand, under the third strand, under the second strand, over the third strand and under the fourth strand; the second strand crosses over the fourth strand, under the first strand, over the third strand, under the fourth strand, over the first strand and under the third strand; the third strand crosses under the fourth strand, over the first stand, under the second strand, over the fourth strand, under the first strand and over the second strand; and the fourth strand crosses under the second strand, over the third strand, under the first strand, over the second strand, under the third strand, and over the first strand, the strands being joined at the proximal and distal end such that the strands are free to adjust their position relative to each other in response to compression forces, wherein the bundle is helically wound to form an elongate coil having a first diameter with the coil being releasably secured to a catheter;
   (c) inserting the catheter into the body vessel;
   (d) advancing the catheter through the body vessel until the coil is positioned at a desired site within the body vessel;
   (e) radially expanding at least a portion of the coil to a second diameter within the body vessel at the desired site such that at least the portion of the coil engages and supports the body vessel, with the second diameter being greater than the first diameter;
   (f) releasing the coil from the catheter; and
   (g) removing the catheter from the body vessel.

9. The method according to claim 8 wherein the first strand comprises a bundle of three strands, the second strand comprises a bundle of three strands, third strand comprises a bundle of three strands and the fourth strand comprises a bundle of three strands.

10. A method for implanting a radially expandable stent within a body vessel, which comprises the steps of:
   (a) providing a stent having at least eight continuous, discrete, metal strands, each strand having a proximal and a distal end;
   (b) arranging the strands in parallel in the following order:
      i) a first strand next to a second strand, next to a third strand, next to a fourth strand, next to a fifth strand, next to a sixth strand, next to a seventh strand, next to an eighth strand, wherein a pattern is repeated such that,
         A) the eighth strand crosses over the seventh strand, under the sixth strand, over the fifth strand, under the fourth strand, over the third strand, under the second strand, over the first strand, over the fourth strand, under the third, over the second and under the first strand;

B) the seventh strand crosses under the eighth strand, over the sixth strand, under the fifth strand, over the fourth strand, under the third strand, over the second strand, under the first strand, over the eighth strand, under the sixth strand, over the fifth strand, under the fourth strand, over the third strand, under the second strand and over the first strand;

C) the sixth strand crosses over the eighth strand, under the seventh strand, over the fifth strand under the fourth strand, over the third strand, under the second strand, over the first strand, under the eighth strand, over the seventh strand, under the fifth, over the fourth strand, under the third strand, over the second strand and under the first strand;

D) the fifth strand crosses under the eighth strand, over the seventh strand, under the sixth strand, over the fourth strand, under the third strand, over the second strand, under the first strand, over the eighth strand, under the seventh strand, over the sixth strand, under the fourth strand, over the third strand, under the second strand and over the first strand;

E) the fourth strand crosses over the eighth strand, under the seventh strand, over the sixth strand, under the fifth strand, over the third strand, under the second strand, over the first strand, under the eighth strand, over the seventh strand, under the sixth strand, over the fifth strand, under the third strand, over the second strand and under the first strand;

F) the third strand crosses under the eighth strand, over the seventh strand, under the sixth strand, over the fifth strand, under the forth strand, over the second strand, under the first strand, over the eighth, under the seventh, over the sixth, under the fifth, over the fourth, under the second and over the first;

G) the second strand crosses over the eighth strand, under the seventh strand, over the sixth strand, under the fifth strand, over the fourth strand, under the third strand, over the first strand, under the eighth strand, over the seventh strand, under the sixth strand, over the fifth strand, under the fourth strand, over the third strand, and under the first strand; and H) the first strand crosses under the eighth strand, over the seventh strand, under the sixth strand, over the fifth strand, under the fourth strand, over the third strand, under the second strand, over the eighth strand, under the seventh strand, over the sixth strand, under the fifth strand, over the fourth strand, under the third strand, over the second strand, over the eighth strand, under the seventh strand, over the sixth strand, under the fifth strand, over the fourth strand, under the third strand and over the second strand;

(c) the strands being joined at the proximal and distal end such that the strands are free to adjust their position relative to each other in response to compression forces, wherein the strands are helically wound to form an elongate coil having a first diameter with the coil being releasably secured to a catheter;

(d) inserting the catheter into the body vessel;

(e) advancing the catheter through the body vessel until the coil is positioned at a desired site within the body vessel;

(f) radially expanding at least a portion of the coil to a second diameter within the body vessel at the desired site such that at least the portion of the coil engages and supports the body vessel, with the second diameter being greater than the first diameter;

(g) releasing the coil from the catheter; and (h) removing the catheter from the body vessel.

* * * * *